United States Patent
Defreitas (10) Patent No.: US 11,703,178 B2
(45) Date of Patent: Jul. 18, 2023

(54) PADDLE STAND

(71) Applicant: Hologic, Inc., Marlborough, MA (US)

(72) Inventor: Kenneth Defreitas, Patterson, NY (US)

(73) Assignee: Hologic, Inc., Marlborough, MA (US)

( * ) Notice: Subject to any disclaimer, the term of this patent is extended or adjusted under 35 U.S.C. 154(b) by 267 days.

(21) Appl. No.: 17/024,872

(22) Filed: Sep. 18, 2020

(65) Prior Publication Data

US 2021/0145375 A1 May 20, 2021

Related U.S. Application Data

(60) Provisional application No. 62/936,919, filed on Nov. 18, 2019.

(51) Int. Cl.
| | |
|---|---|
| *F16M 11/42* | (2006.01) |
| *F16M 11/00* | (2006.01) |
| *F16M 13/00* | (2006.01) |
| *A47B 96/14* | (2006.01) |
| *A47B 96/06* | (2006.01) |
| *A47B 57/18* | (2006.01) |

(52) U.S. Cl.
CPC ........... *F16M 11/42* (2013.01); *A47B 96/063* (2013.01); *A47B 96/1416* (2013.01); *A47B 96/1466* (2013.01); *F16M 11/00* (2013.01); *F16M 13/00* (2013.01); *A47B 57/18* (2013.01)

(58) Field of Classification Search
CPC ........ F16M 11/42; F16M 11/00; F16M 13/00; F16M 2200/08; A61B 6/025; A61B 6/0414; A61B 6/502; A47K 10/04; Y10S 248/91; A47F 5/06; A47F 5/04; A47B 96/1483; A47B 96/1466; A47B 57/18; A47B 96/1416; A47B 57/565; A47B 96/063; A47B 96/065

See application file for complete search history.

(56) References Cited

U.S. PATENT DOCUMENTS

| | | | | |
|---|---|---|---|---|
| 883,323 | A * | 3/1908 | Macduff .............. | A47B 96/027 |
| | | | | 211/90.01 |
| 2,901,206 | A * | 8/1959 | Gredell .................. | A47B 57/56 |
| | | | | 248/246 |
| RE27,186 | E * | 10/1971 | Ferdinand et al. .... | A47B 57/44 |
| | | | | 108/107 |
| 3,897,037 | A * | 7/1975 | Johnson ............... | A47B 23/042 |
| | | | | 248/452 |
| 4,733,843 | A * | 3/1988 | Bessinger ............ | A47B 96/065 |
| | | | | 211/90.01 |
| 4,821,892 | A * | 4/1989 | Randall ................ | A47B 96/063 |
| | | | | 211/90.01 |

(Continued)

FOREIGN PATENT DOCUMENTS

WO    WO-2016073445 A1 *    5/2016    ............ A61B 6/025

*Primary Examiner* — Ko H Chan
(74) *Attorney, Agent, or Firm* — Merchant & Gould P.C.

(57) ABSTRACT

An apparatus for holding a breast compression paddle, includes a base, a lip connected to and extending substantially orthogonal from the base, an arm connected to and extending substantially orthogonal from the base and disposed substantially parallel to the lip, and a tine connected to and extending at an angle to the arm. The lip defines a lip plane, and the tine is oriented towards the lip plane. The apparatus is configured to hold and support a compression paddle.

17 Claims, 8 Drawing Sheets

(56) References Cited

U.S. PATENT DOCUMENTS

| | | | | |
|---|---|---|---|---|
| 4,895,331 | A * | 1/1990 | Nehls | A47B 57/565 |
| | | | | 248/245 |
| 4,934,642 | A * | 6/1990 | Baron | A47B 96/065 |
| | | | | 211/90.01 |
| 5,354,025 | A * | 10/1994 | McCaffrey | A47B 57/44 |
| | | | | 211/187 |
| 6,776,466 | B2 * | 8/2004 | Harvie, III | A47B 96/061 |
| | | | | 312/351 |
| 7,178,765 | B2 * | 2/2007 | Huang | A47B 21/00 |
| | | | | 52/36.6 |
| 7,347,404 | B2 * | 3/2008 | Anzai | A47F 5/0853 |
| | | | | 248/250 |
| 7,665,701 | B2 * | 2/2010 | Mitterbacher | E04F 13/0808 |
| | | | | 248/231.91 |
| 8,186,524 | B2 * | 5/2012 | Siahpush | A47F 7/283 |
| | | | | 211/133.4 |
| 8,561,820 | B2 * | 10/2013 | Kitt | A61G 12/001 |
| | | | | 211/187 |
| 8,967,402 | B2 * | 3/2015 | Pintur | A47B 47/022 |
| | | | | 211/DIG. 1 |
| 9,326,600 | B1 * | 5/2016 | Reynolds | A47B 96/021 |
| 10,925,178 | B2 * | 2/2021 | Tanguay | H05K 7/18 |
| 11,083,286 | B2 * | 8/2021 | Seyfried | F16B 1/00 |
| 11,297,962 | B2 * | 4/2022 | Palmer | A47G 19/08 |
| 2006/0054752 | A1 * | 3/2006 | Huang | F16M 13/02 |
| | | | | 248/125.1 |
| 2012/0292275 | A1 * | 11/2012 | Duquette | A47B 96/063 |
| | | | | 211/90.01 |

\* cited by examiner

FIG.6C

PADDLE STAND

CROSS-REFERENCE TO RELATED APPLICATIONS

This application claims priority to, and the benefit of, U.S. Provisional Patent Application No. 62/936,919, filed Nov. 18, 2019, the disclosure of which is hereby incorporated by reference herein in its entirety.

BACKGROUND

Mammography and tomosynthesis imaging are common medical procedures for detecting potential areas of interest in the breasts of a patient. Typically, an imaging system is located in an imaging suite of a hospital or doctor's office. A number of compression paddles may be used interchangeably with the imaging system to accommodate breast of various sizes and/or to perform particular procedures (e.g. image-guided biopsy). For example, paddles may be designed for small or large breasts. Other paddles, such as foam or partial foam paddles may be used to stabilize the breast without causing excessive compression (and the attendant discomfort). Biopsy procedures may require paddles that include a window or opening therein for penetration of a biopsy needle. Other paddles may include flexible plastic coverings or may be shaped to be more comfortable. To accommodate a greater number of patients and procedures, a number of the various types of paddles must be available to a technician when using the imaging system.

SUMMARY

In one aspect, the technology relates to an apparatus for holding a breast compression paddle, the apparatus including: a base defining at least one opening; a lip connected to and extending substantially orthogonal from the base, wherein the lip defines a lip plane; an arm connected to and extending substantially orthogonal from the base and disposed substantially parallel to the lip; and a tine connected to and extending at an angle to the arm, wherein the tine is oriented towards the lip plane. In an example, the opening includes a plurality of openings. In another example, a first opening of the plurality of openings is defined on a first side of the lip plane, and wherein a second opening of the plurality of openings is defined on a second side of the lip plane. In yet another example, the lip extends a first distance from the base and the arm extends a second distance from the base, wherein the second distance is greater than the first distance. In still another example, the lip extends along an entire length of the base.

In another example of the above aspect, the lip includes a plurality of lips. In an example, the lip includes a plurality of projections. In another example, the arm includes a plurality of arms. In yet another example, the tine includes a plurality of tines, and wherein one tine of the plurality of tines is connected to each arm of the plurality of arms. In still another example, the apparatus includes a unitary part.

In another aspect, the technology relates to an apparatus for holding a breast compression paddle, the apparatus including: a vertical post including a plurality of sides, wherein at least one side of the plurality of sides at least partially defines a slot; a bracket including: a base; a lip connected to and extending from the base; an arm connected to and extending from the base and disposed substantially parallel to the lip; a tine connected to and extending at an angle to the arm; and a fastener for releasably connecting the bracket to the post at the slot. In an example, the base defines at least one opening for receiving the fastener, and wherein the fastener is a bolt. In another example, the apparatus further includes a nut slidably disposed in the slot, and wherein the bolt is releasably secured to the nut. In another example, the slot includes a pair of parallel slots. In yet another example, the post includes four sides and wherein each of the four sides defines a pair of parallel slots. In still another example, the bracket includes a plurality of brackets.

In another example of the above aspect, one bracket of the plurality of brackets is secured to each side of the post. In yet another example, the apparatus includes a base stand for supporting the post. In still another example, the apparatus includes a plurality of wheels connected to the base stand for rolling the apparatus along a surface.

In another aspect, the technology relates to a method of storing a breast compression paddle including a connection bracket, wherein the connection bracket includes an edge and defines at least one opening, the method including: providing the breast compression paddle; inverting the breast compression paddle; after inverting the breast compression paddle, inserting the edge of the breast compression paddle into a lip of a storage bracket; inserting a tine of the storage bracket into the at least one opening; and disposing the connection bracket on the storage bracket.

DETAILED DESCRIPTION

Figure 1:
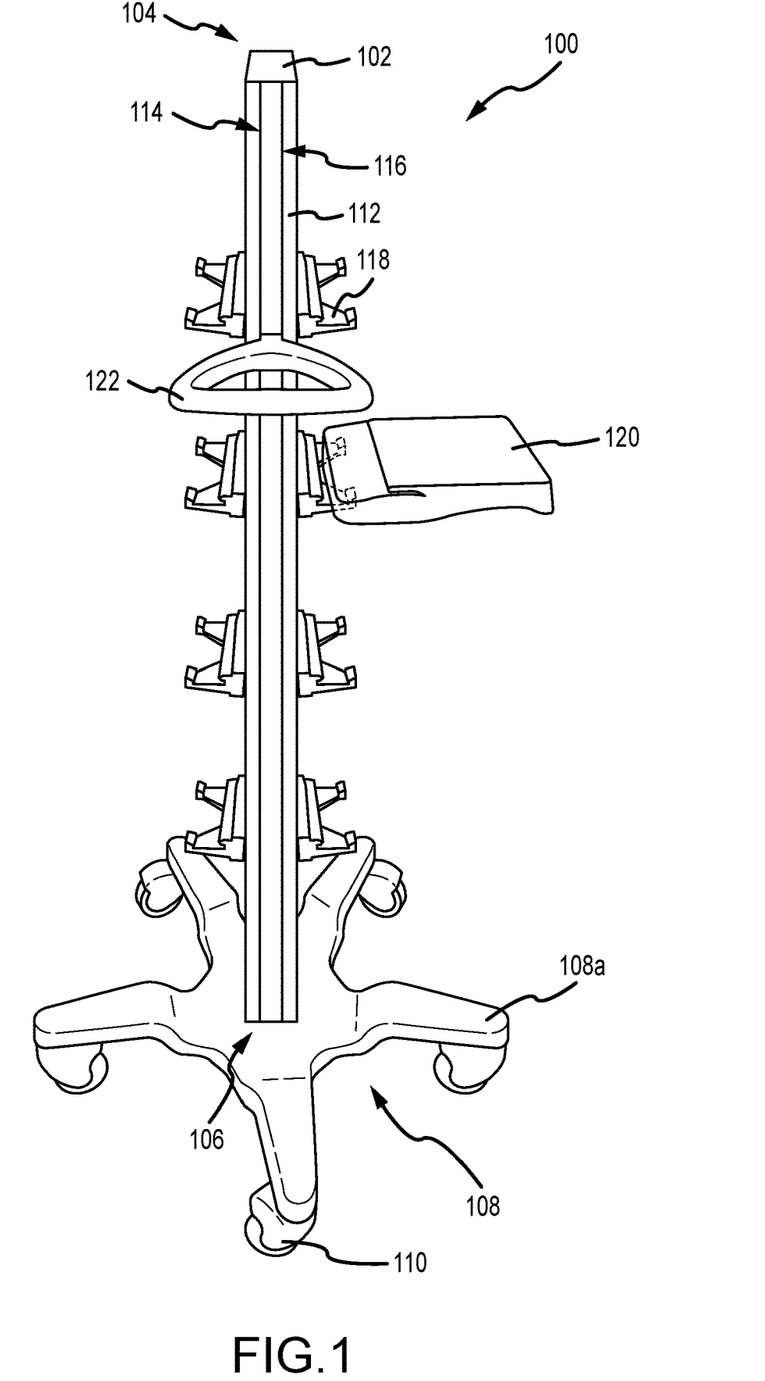
FIG. 1 is a perspective view of a movable paddle storage stand.

FIG. 1 is a perspective view of a movable paddle storage stand 100. The stand 100 includes an elongate, upright post 102 having an upper end 104 and a lower end 106. The lower end 106 may be connected to a base stand 108 having a plurality of legs 108a to maintain stability of the stand 100. The stand 100 may be generally static, and in such a case would include a number of feet (e.g., one per leg 108a) having a rubberized or other high-friction material to prevent inadvertent sliding of the stand 100. In this example, however, each leg 108a includes a roller, caster, or other wheel 110 connected thereto. This allows the stand 100 to be moved more easily around a hospital or imaging suite. The post 102 includes a number of sides 112, four in this example, a greater or lesser number of sides may be utilized, but four may be a common commercial configuration.

Each side 112 defines one or more elongate slots 114, 116, which may extend from the upper end 104 to the lower end 106 of the post 102. In other examples, the slots 114, 116 may extend along a portion of the entire length of the post 102. In other examples, only a single slot per side 112 may be utilized, though in such a configuration, the slot may be centered on each side 112. The slots 114, 116 act as an energizing structure for a number of brackets 118, which may be arranged along the length of the post 102, on one or more sides 112 thereof. Each bracket 118 may be used to support a compression paddle 120, of various configurations, as known in the art. Each paddle 120 is supported on the bracket 118 in an inverted orientation, e.g., with the compressive surface facing upward. During imaging procedures, of course, compression paddles are disposed in an upright orientation, with the compressive surface facing down. By supporting the paddles 120 in the inverted orientation, features of each paddle 120 are more readily apparent to a technician, so the technician may quickly select the appropriate paddle 120 for a particular patient or procedure. A handle 122 is also secured to the post 102, either directly or at one or more of the slots 114, 116, so as to enable the stand 100 to be more easily manipulated within an environment.

Figure 2:
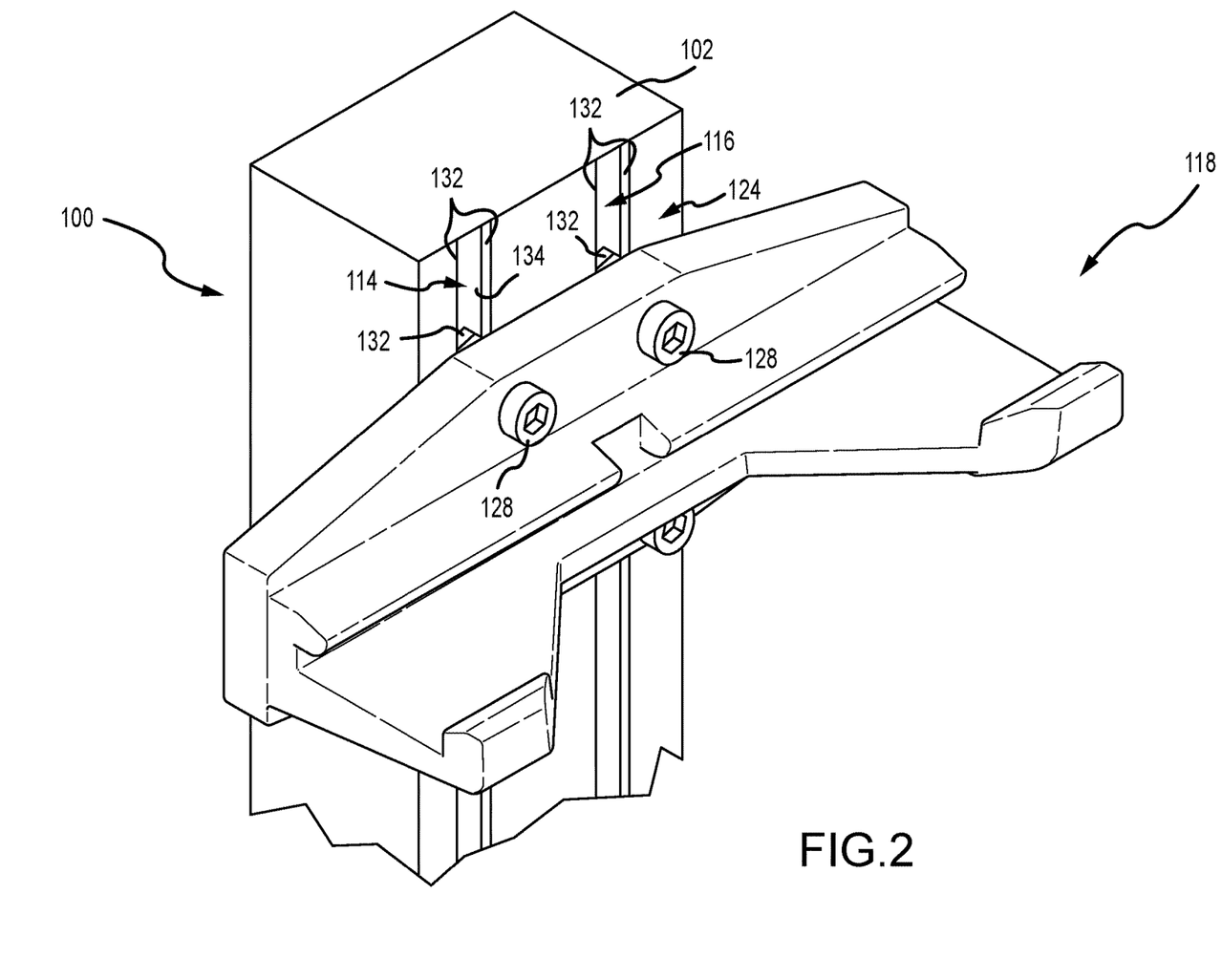
FIG. 2 is an enlarged partial perspective view of a paddle storage stand.
Figure 3:
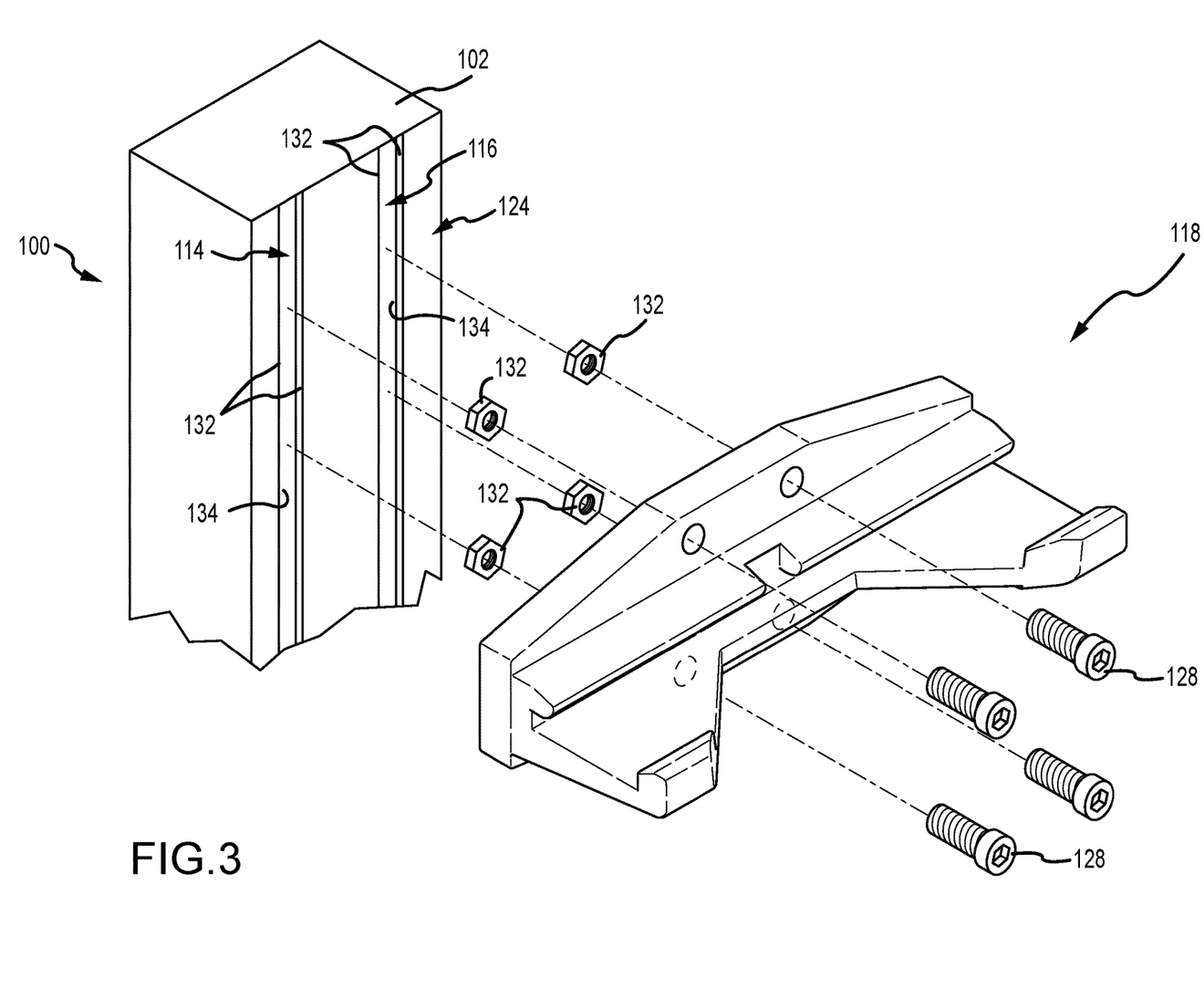
FIG. 3 is an enlarged exploded partial perspective view of a paddle storage stand.

FIG. 2 is an enlarged partial perspective view of a paddle storage stand 100, while FIG. 3 is an enlarged exploded partial perspective view of a paddle storage stand 100. FIGS. 2 and 3 are described concurrently. Each side 112 includes a surface 124 that may be smooth or textured. A textured surface, while not required, may increase frictional contact between a bracket 118 and the surface 124, which may help retain the bracket 118 in the desired location. The bracket 118 is a generally unitary body 126 that may be molded, cast, or machined, as required or desired depending on the material utilized. A plurality of fasteners 128 are used to secure the bracket to the post 102. In this example, the fasteners 128 are bolts, although screws or other anchors may be used. In the case of a bolt 128, an outer washer (not shown) may be used to distribute forces of the bolt 128 on the bracket 118. The bolt 128 is engaged with a nut 132 that is sized to slide vertically within the slot 114, 116. A pair of lips defining the throat 134 of each slot 114, 116 prevents the nut 132 from being pulled through the throat 134. Thus, to move a bracket 118 up or down along the post 102, a user may loosen slightly the fastener(s) 128 present, slide the bracket 118 up or down to the desired location, then retighten the fastener(s) 128. The ability to slide the brackets 118 up and down along the post allows a user to configure the paddle storage stand 100 to hold as many paddles as required or desired. Brackets 118 for holding relatively thin paddles (basic rigid plastic paddles), for example, may be placed closer together than brackets for holding relatively thick paddles (paddles including thick foam components). FIG. 2 depicts a compression paddle 120 supported by the bracket 118. In another example, a surface of the paddle storage stand 100 opposite the front surface 124 may abut a building structure such as a wall so the stand 100 may be secured directly thereto (of course, in a such a configuration, no base stand would be present).

Figure 4:
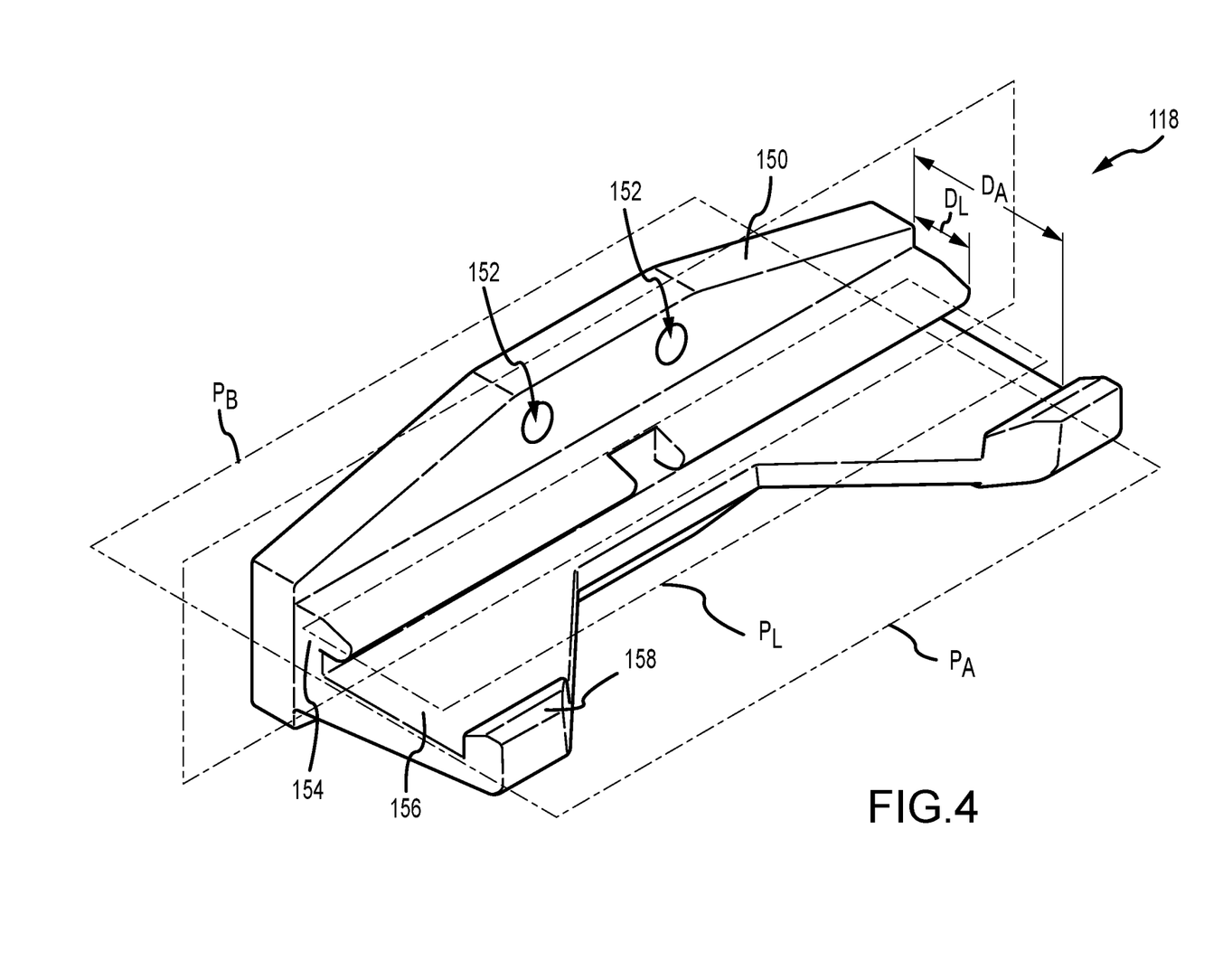
FIG. 4 is a perspective view of a bracket for a paddle storage stand.

FIG. 4 is a perspective view of a bracket 118 for a paddle storage stand. The bracket 118 includes a base 150 that defines a plurality of openings 152 for receipt of the fasteners described elsewhere herein. In examples, openings may be disposed above and/or below a lip 154. The lip 154 is connected to and extends from the base 150 a distance DL. In the depicted example, the lip 154 includes two discrete portions or lips that, together, extend along nearly the entire width of the base 150. In other examples, the lip may extend along a portion thereof. In yet another example, the lip may be one or more projections that simply extend a predetermined distance from the base 150. The lip 154 need only extend a distance DL sufficient to provide a feature that may engage with an edge of a compression paddle (not shown). Also connected to and extending from the base 150 are one or more arms 156. The arms 156 extend a distance DA from the base 150, which may be greater than the distance DL. When a compression paddle is engaged with the bracket 118, the arms 156 support the compression paddle, proximate or on a connection bracket thereof. Each arm 156 terminates at a tine 158. The tine 158 may be enlarged and is configured to project into an opening defined by the connection bracket of the compression paddle, as described in more detail herein.

The various elements of the bracket 118 are arranged so as to easily support a number of compression paddles while occupying a minimal footprint. Floor space within most imaging suites is at a premium, however, a significant number of different types of paddles are often required for each suite. Such paddles are specifically designed for various purposes and patients (e.g., paddles for biopsy, paddles for imaging large breasts, paddles for imaging small breast, foam paddles for stabilizing breast with minimal compression, flat paddles, curved paddles, pivoting paddles, etc.). Thus, the significant number and type of paddles must be both available in each suite and organized. The paddle stand depicted and described herein enhances both availability and organization. By placing the paddles on a movable stand, access is further improved for the imaging technician, who is able to move the stand to different locations as required or desired to improve efficiency of workflow. Further, while a number compression paddles could simply be supported loosely on a large flat shelf, the configuration of movable paddle stand depicted and described herein allows for improved, high-density, and stable storage of various paddles. The configuration of the bracket 118 described herein provides the minimum required support, both from below and laterally, so as to prevent the compression paddle from being easily dislodged from the bracket 118, for example, as the stand is rolled around an imaging suite, or as other paddles are removed from or placed on the stand, which may cause bumping interference with adjacent paddles. In the depicted example, the features of the bracket may be defined by a number of planes. For example, the base 150 may define a base plane $P_B$ that, when the bracket 150 is secured to a post of a paddle stand, is disposed substantially vertically. The lip 154 may define a lip plane $P_L$ that extends away from the base plane $P_B$. In the depicted example, the lip plane $P_L$ may be disposed substantially orthogonal to the base plane $P_B$. In other examples, the lip plane $P_L$ may be disposed at an angle to the base plane $P_B$ (e.g., so the lip 154 points generally upward). The arm 156 may define an arm plane $P_A$ that also extends from the base plane $P_B$. As depicted in FIG. 4, the arm plane $P_A$ is generally parallel to the lip plane $P_L$. In examples where the lip plane $P_L$ points generally upward, the arm plane $P_A$ may be similarly oriented.

It has been determined that most compression paddles stored on the paddle stand may simply rest on the arm 156, with an edge of the compression paddle disposed under the lip 154 (e.g., between the lip 154 and the arm 156). The weight of the paddle pulls the paddle downward, thus engaging the edge thereof with the lip 154. This engagement is often sufficient to hold the paddle in place. However, it may be advantageous to include the depicted tines 158, which prevent lateral movement of the paddle, which may occur as the paddle stand is rolled around an environment. The tines 158 extend at an angle to the arm plane $P_A$, and in some cases may be disposed substantially vertically. Regardless, the tines are generally oriented in the direction of the lip plane $P_L$. The tines 158, so disposed, project into the apertures in a connection bracket of the compression paddle. This engagement prevents the compression paddle from being pulled away from the bracket 118, or sliding laterally along the arms 156 of the bracket 150.

Figure 5:
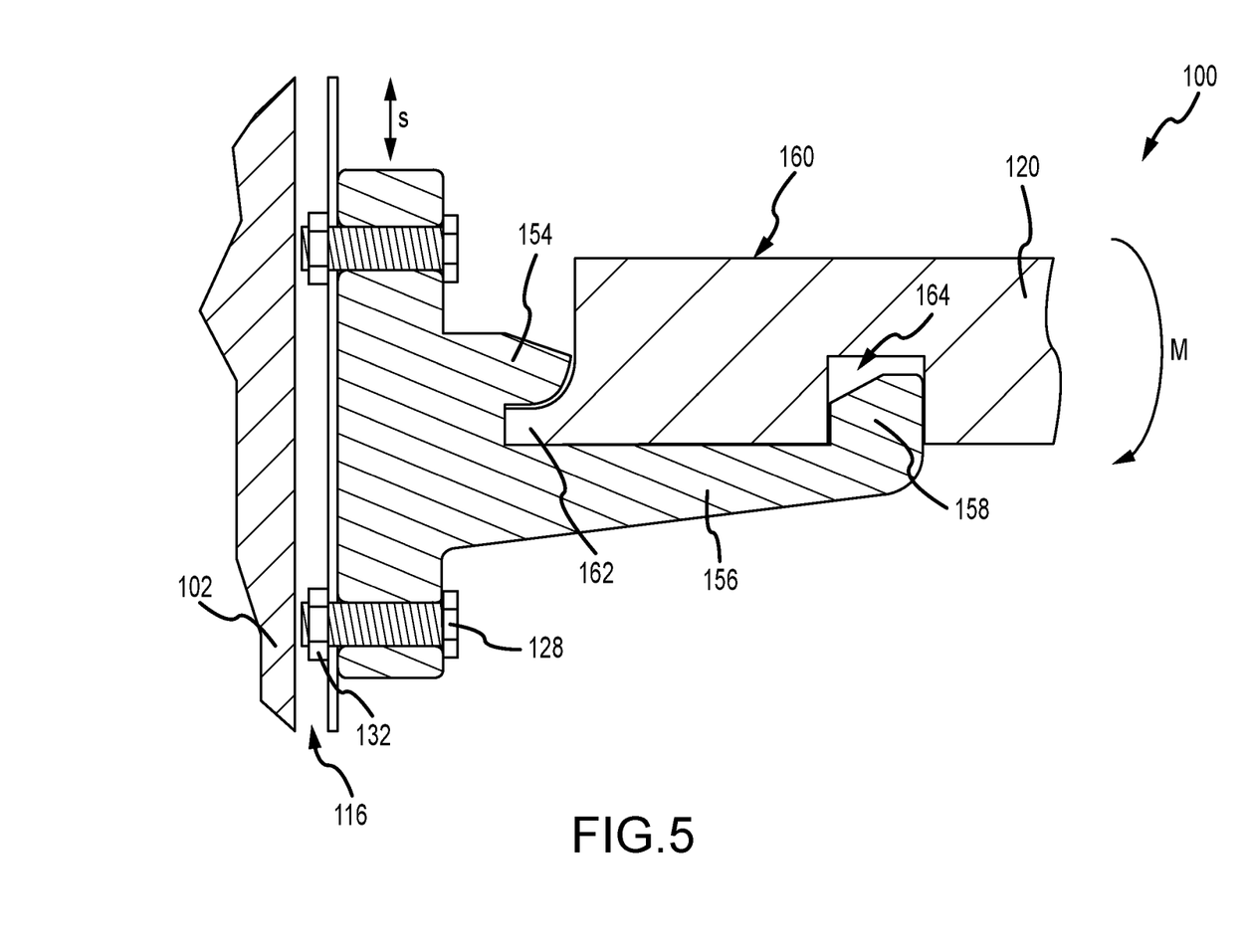
FIG. 5 is a partial sectional view of compression paddle engaged with a bracket of a paddle storage stand.

FIG. 5 is a partial sectional view of compression paddle 120 engaged with a bracket 118 of a paddle storage stand 100. The compression paddle 120 includes a connection bracket 160, that is, the portion of the compression paddle 120 that is used to secure the paddle 120 to a compression arm of an imaging system. The paddle 120 includes an edge 162 extending therefrom and an aperture 164 is defined in the connection bracket 160. The connection bracket 160 rests on the arm 156 such that the edge 162 extends between the arm 156 and the lip 154 of the bracket 118. The compression paddle 120 is thus cantilevered away from the bracket 118. A moment M is applied about the tine 158 (located at the end of the arm 156) and countered by engagement between the edge 162 and the lip 154. The tine 158 extends into the opening 164 of the compression paddle 120, so as to prevent the compression paddle 120 from being inadvertently dislocated. The bolt 128 is connected to the nut 132 disposed within the slot 116. By loosening the bolt 128 from the nut 132, the bracket 118 may be slid S up or down along the post 102.

Figure 6A:
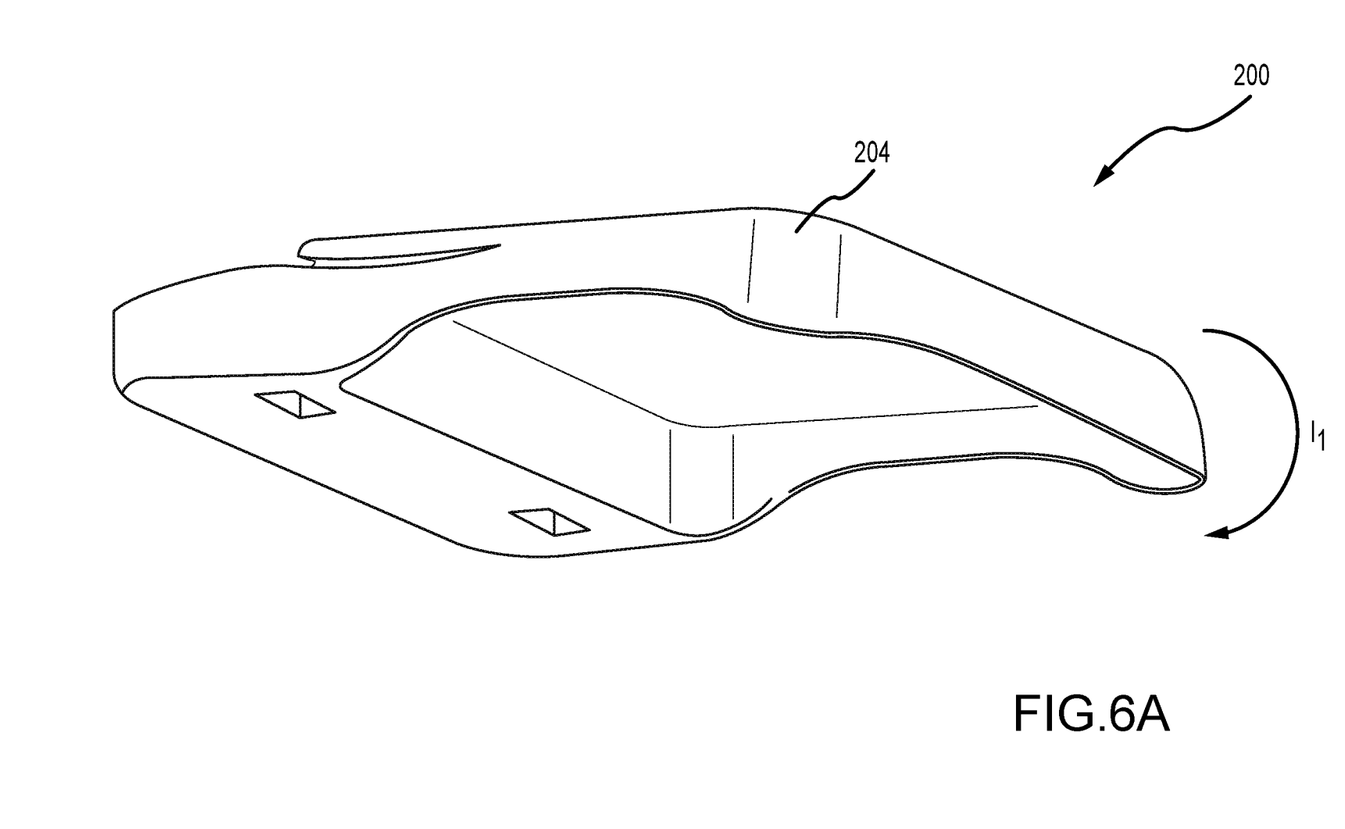
FIGS. 6A-6C depict a method of using a paddle storage stand.
Figure 6B:
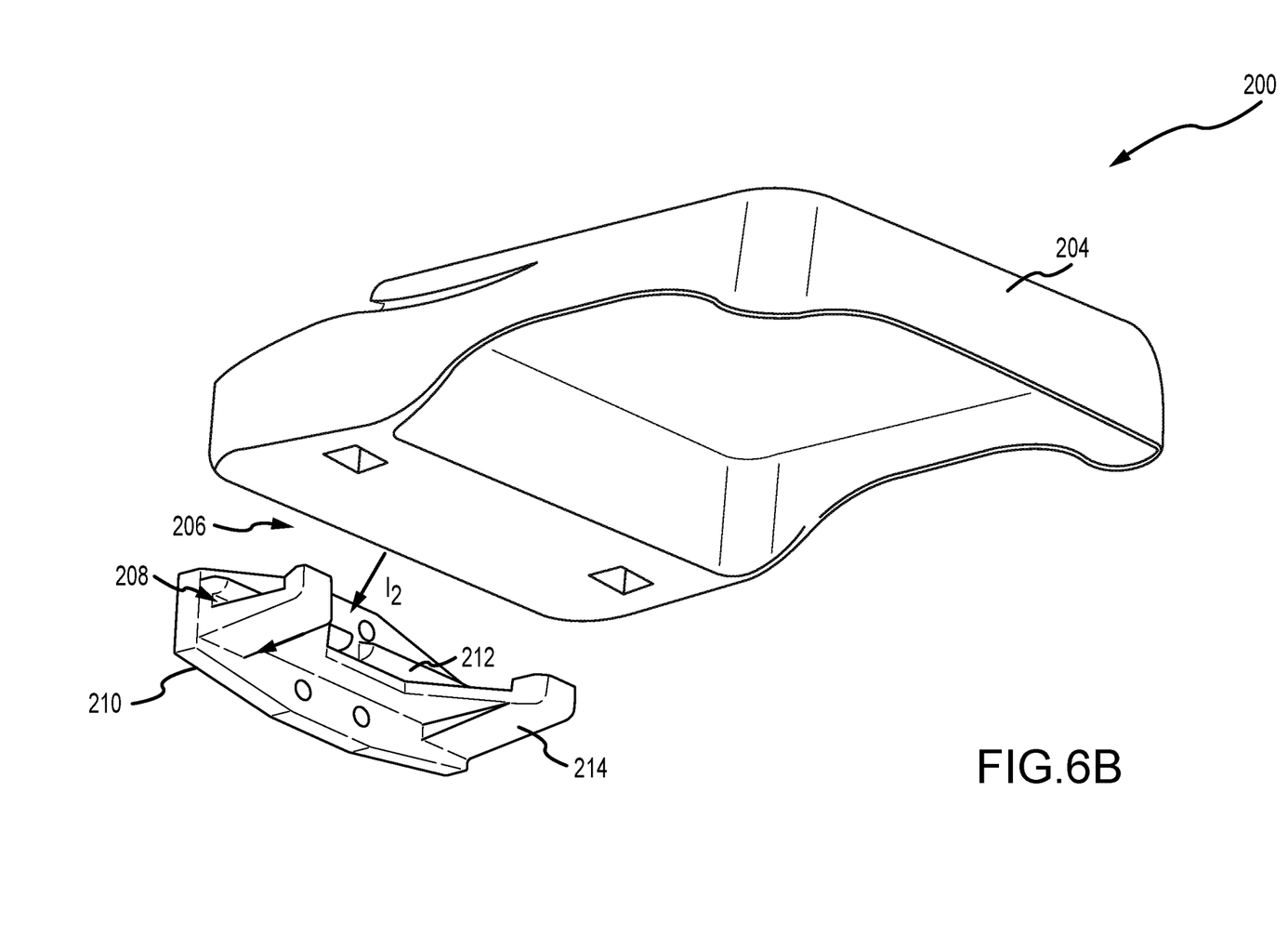
Figure 6C:
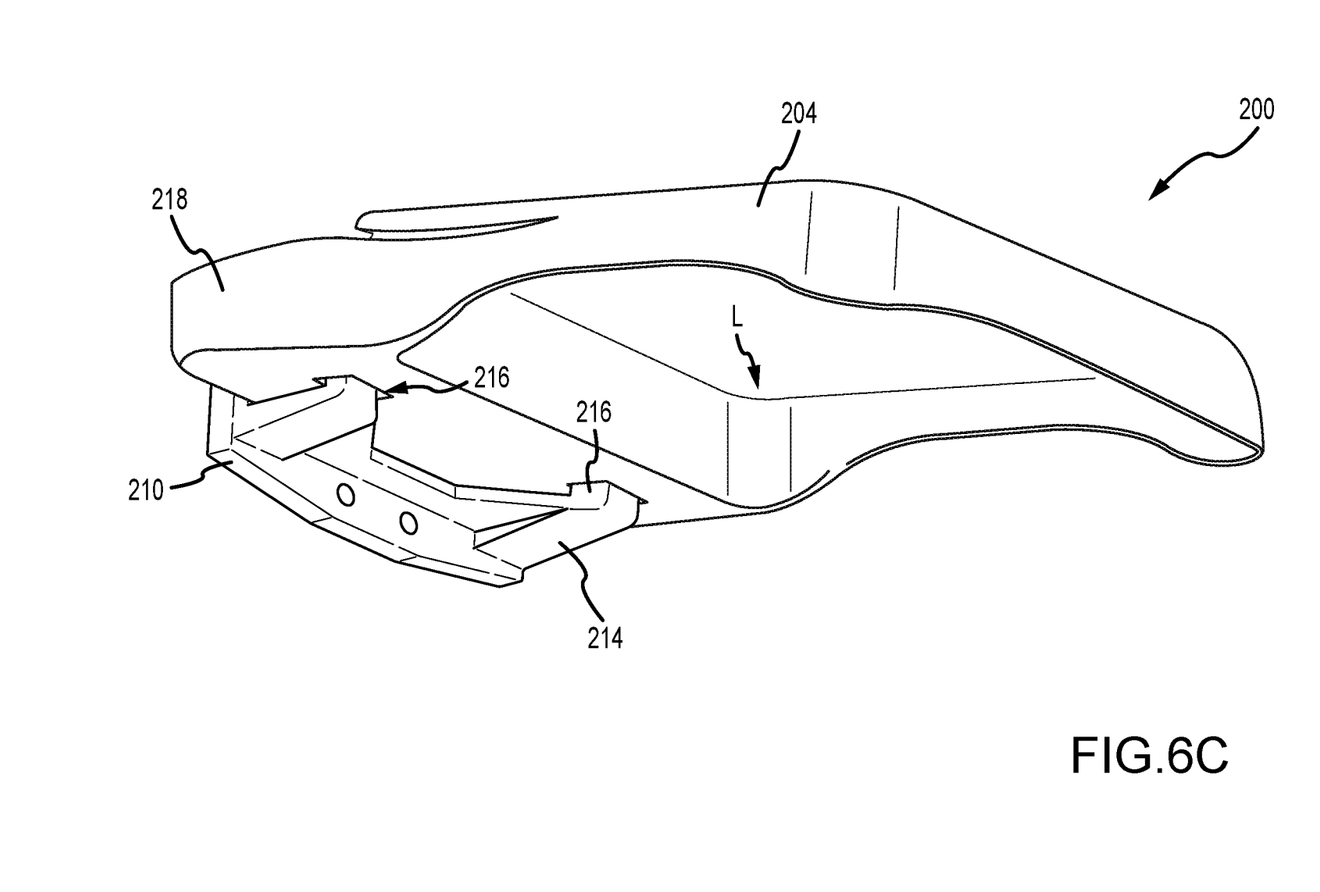

FIGS. 6A-6C depict a method 200 of using a paddle storage stand (not shown). FIG. 6A depicts a breast compression paddle 204. The breast compression paddle 204 may have been removed from an imaging system (not shown) or may have recently been received in the imaging center (e.g., either shipped from a manufacturer or provided by the facility in which the imaging system is located). The compression paddle 204 is first inverted Ii from an upright orientation to an inverted orientation. FIG. 6B depicts insertion 12 of a portion of the breast compression paddle 204 (e.g., an edge 206) into a recess 208 of a bracket 210. In the depicted example, the recess 208 is defined between a lip 212 and an arm 214 of the bracket 210. FIG. 6C depicts lowering L of the compression paddle 204, such that a tine 216 of the bracket 210 is received within an opening 216 of the bracket 210. The opening 216 is formed in a connection bracket portion 218 of the compression paddle 204 (e.g., the portion of the paddle 204 that connects the compression paddle 204 to a compression arm of an imaging system). Once lowered L, the connection bracket portion 218 of the paddle 204 rests on the arm 214.

The brackets described herein may be cast, molded, or machined, as a unitary whole or in a number of parts joined during manufacturing, as required or designed for a particular application. In examples, metals such as cast aluminum may be utilized. Robust plastics, e.g. carbon reinforced plastics or otherwise, may be utilized. In examples, the brackets depicted herein may be manufactured for materials similar to those used to manufacture compression paddles. The paddle stand may be manufactured for similar materials, as well as materials used for other medical equipment.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. An apparatus for holding a breast compression paddle comprising an edge and pair of openings on an upper surface of the breast compression paddle, the apparatus comprising:
   a base defining at least one opening;
   a lip connected to and extending substantially orthogonal from the base, wherein the lip extends a first distance from the base and defines a lip plane;
   a first arm connected to and extending substantially orthogonal from the base to a second distance greater than the first distance and disposed substantially parallel to and spaced apart from and below the lip so as to define a first gap therebetween;
   a first tine connected to a terminal end of the first arm opposite the base and extending at an angle to the terminal end of the first arm, wherein the tine is oriented upward towards the lip plane, so as to penetrate a first opening of the pair of openings on the breast compression paddle;
   a second arm connected to and extending substantially orthogonal from the base to the second distance and disposed substantially parallel to and spaced apart from and below the lip so as to define a second gap therebetween, and wherein the first gap and the second gap are configured to receive the edge of the breast compression paddle; and
   a second tine connected to a terminal end of the second arm opposite the base and extending at an angle to the terminal end of the second arm, wherein the tine is oriented upward towards the lip plane, so as to penetrate a second opening of the pair of openings on the breast compression paddle,
      wherein when the edge is received within the first gap and the second gap, and wherein when the first tine is penetrating the first opening and the second tine is penetrating the second opening, the breast compression paddle is cantilevered away from the base.

2. The apparatus of claim 1, wherein the opening comprises a plurality of openings.

3. The apparatus of claim 2, wherein a first opening of the plurality of openings is defined on a first side of the lip plane, and wherein a second opening of the plurality of openings is defined on a second side of the lip plane.

4. The apparatus of claim 1, wherein the lip extends along an entire length of the base.

5. The apparatus of claim 1, wherein the lip comprises a plurality of lips.

6. The apparatus of claim 1, wherein the lip comprises a plurality of projections.

7. The apparatus of claim 1, wherein the apparatus comprises a unitary part.

8. An apparatus for holding a breast compression paddle comprising an edge and pair of openings on an upper surface of the breast compression paddle, the apparatus comprising:
   a vertical post comprising a plurality of sides, wherein at least one side of the plurality of sides at least partially defines a slot;
   a bracket comprising:
      a base defining at least one opening;

a lip connected to and extending substantially orthogonal from the base, wherein the lip extends a first distance from the base and defines a lip plane;

a first arm connected to and extending substantially orthogonal from the base to a second distance greater than the first distance and disposed substantially parallel to and spaced apart from and below the lip so as to define a first gap therebetween;

a first tine connected to a terminal end of the first arm opposite the base and extending at an angle to the terminal end of the first arm, wherein the tine is oriented upward towards the lip plane, so as to penetrate a first opening of the pair of openings on the breast compression paddle;

a second arm connected to and extending substantially orthogonal from the base to the second distance and disposed substantially parallel to and spaced apart from and below the lip so as to define a second gap therebetween, and wherein the first gap and the second gap are configured to receive the edge of the breast compression paddle; and a second tine connected to a terminal end of the second arm opposite the base and extending at an angle to the terminal end of the second arm, wherein the tine is oriented upward towards the lip plane, so as to penetrate a second opening of the pair of openings on the breast compression paddle, wherein when the edge is received within the first gap and the second gap, and wherein when the first tine is penetrating the first opening and the second tine is penetrating the second opening, the breast compression paddle is cantilevered away from the base; and a fastener for releasably connecting the bracket to the post at the slot.

9. The apparatus of claim 8, wherein the base defines the at least one opening for receiving the fastener, and wherein the fastener is a bolt.

10. The apparatus of claim 8, further comprising a nut slidably disposed in the slot, and wherein the bolt is releasably secured to the nut.

11. The apparatus of claim 8, wherein the slot comprises a pair of parallel slots.

12. The apparatus of claim 8, wherein the post comprises four sides and wherein each of the four sides defines a pair of parallel slots.

13. The apparatus of claim 12, wherein the bracket comprises a plurality of brackets.

14. The apparatus of claim 13, wherein one bracket of the plurality of brackets is secured to each side of the post.

15. The apparatus of claim 8, further comprising a base stand for supporting the post.

16. The apparatus of claim 15, further comprising a plurality of wheels connected to the base stand for rolling the apparatus along a surface.

17. A method of storing a breast compression paddle comprising a connection bracket, wherein the connection bracket comprises an edge and defines at least one opening, the method comprising:

providing the breast compression paddle;

inverting the breast compression paddle;

after inverting the breast compression paddle, inserting the edge of the breast compression paddle between an arm and a lip of a storage bracket;

inserting a tine of the storage bracket into the at least one opening, wherein the tine extends from the arm; and disposing the connection bracket on the storage bracket.

* * * * *